US008431739B2

(12) United States Patent
Divi et al.

(10) Patent No.: US 8,431,739 B2
(45) Date of Patent: Apr. 30, 2013

(54) PROCESS FOR THE PREPARATION OF GABAPENTIN

(75) Inventors: Murali Krishna Prasad Divi, Hyderabad (IN); Gundu Rao Padakandla, Hyderabad (IN); Mysore Aswatha Narayana Rao, Hyderabad (IN); Shaik Nowshuddin, Hyderabad (IN); Maddipati Prasad, Hyderabad (IN)

(73) Assignee: Divi's Laboratories, Ltd. (IN)

( * ) Notice: Subject to any disclaimer, the term of this patent is extended or adjusted under 35 U.S.C. 154(b) by 407 days.

(21) Appl. No.: 12/967,447

(22) Filed: Dec. 14, 2010

(65) Prior Publication Data
US 2011/0306787 A1 Dec. 15, 2011

(30) Foreign Application Priority Data

Jun. 14, 2010 (IN) .......................... 1640/CHE/2010

(51) Int. Cl.
*C07C 227/38* (2006.01)

(52) U.S. Cl.
USPC ....................................................... 562/507

(58) Field of Classification Search ........................ None
See application file for complete search history.

(56) References Cited

U.S. PATENT DOCUMENTS

| 4,024,175 A | 5/1977 | Satzinger et al. |
| 4,152,326 A | 5/1979 | Hartenstein et al. |
| 4,894,476 A | 1/1990 | Butler et al. |
| 5,091,567 A | 2/1992 | Geibel et al. |
| 5,998,402 A | 12/1999 | Miller |
| 6,255,526 B1 | 7/2001 | Pesachovich et al. |
| 7,196,216 B2 | 3/2007 | Saigal et al. |
| 7,439,387 B2 | 10/2008 | Satyanarayana et al. |
| 7,635,717 B2 | 12/2009 | Kuppuswamy et al. |
| 2006/0149099 A1 | 7/2006 | Kuppuswamy et al. |

FOREIGN PATENT DOCUMENTS

| EP | 0082183 A1 | 10/1997 |
| WO | 2008098527 A1 | 8/2008 |

OTHER PUBLICATIONS

Chris P. Miller, et al. Design, Synthesis, and Preclinical Characterization of Novel, Highly Selective Indole Estrogens, Journal of Medicinal Chemistry, vol. 44, p. 1654-1657 Feb. 27, 2001.

*Primary Examiner* — Yevegeny Valenrod
(74) *Attorney, Agent, or Firm* — Caesar, Rivise, Bernstein, Cohen & Pokotilow, Ltd.

(57) ABSTRACT

This invention discloses a process for converting gabapentin acid salt to free gabapentin, where the salt is dissolved in an organic solvent in which both gabapentin acid salt and free gabapentin are soluble. The solution is treated with a powdered alkaline base to liberate free gabapentin which will remain in solution. The insoluble alkali salt of the acid is removed by filtration. From the filtrate free gabapentin is obtained either by adding anti-solvent or by extraction with water.

12 Claims, No Drawings

PROCESS FOR THE PREPARATION OF GABAPENTIN

CROSS-REFERENCE TO RELATED APPLICATIONS

This application claims priority from India Application Serial No 1640/CHE/2010, filed on Jun. 14, 2010, entitled Process for the Preparation of Gabapentin, which application is assigned to the same assignee as this application and whose disclosure is incorporated by reference herein.

FIELD OF THE INVENTION

The present invention relates to a new process for converting gabapentin acid salts to gabapentin.

BACKGROUND OF THE INVENTION

Gabapentin is chemically, 1-(aminomethyl)-1-cyclohexane acetic acid, having the structure shown below:

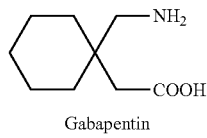 [SMILES: NCC1(CC(=O)O)CCCCC1]

Gabapentin

Gabapentin is useful in treating epilepsy and various other cerebral disorders. It was first described by Warner-Lambert Co. in U.S. Pat. No. 4,024,175.

Several processes for the preparation of gabapentin are reported in the literature. U.S. Pat. No. 4,024,175 describes three methods to prepare gabapentin. All the methods result in gabapentin hydrochloride salt, which is converted to free gabapentin by treatment with a basic ion-exchange resin. U.S. Pat. No. 4,894,476 discloses a hydrated gabapentin which is prepared by liberating the free gabapentin base from its hydrochloride salt by pouring the salt solution onto a column of ion exchange resin like Amberlite IRA-68, eluting with deionised water and further work up to recover the hydrated form. U.S. Pat. No. 5,091,567 discloses the conversion of the gabapentin hydrochloride salt to gabapentin base by passing through a weakly basic anion exchanger. Gabapentin is manufactured in ton lot quantities and a preparative column chromatography is not convenient for applications on an industrial scale. It requires long time and results in a large volume of aqueous solution to be evaporated at low temperature, which makes the process cumbersome and uneconomical.

A process for the conversion of gabapentin hydrochloride to free gabapentin is described in the U.S. Pat. No. 6,255,526 B1. In this process, gabapentin hydrochloride is dissolved in a solvent such as ethyl acetate, in which free gabapentin is insoluble. An alkyl amine such as tributylamine is added to precipitate gabapentin, which is insoluble in the solvent and is recovered by filtration. Alkyl amine hydrochloride, formed in the reaction being soluble in the solvent, will remain in solution. Here, gabapentin is obtained as Form III and again has to be converted to Form II, which is the generic form. In addition to ethylacetate, the patent also mentions benzyl alcohol as a solvent and gives 43% yield of gabapentin (Table-1, Example 11). It is clear that only 43% gabapentin precipitates out from the solution and the remaining 57% remains in the solution. With only 43% yield, the process is uneconomical. Thus, benzyl alcohol is not a suitable solvent for this process.

U.S. Pat. No. 7,439,387 B2 describes the conversion of gabapentin hemisulphate salt to free gabapentin by treating with alkyl amines such as triethylamine or diisopropyl ethyl amine. In all these cases, the alkyl amines used are nonvolatile liquids and are difficult to remove, requiring repeated extractions.

U.S. Pat. No. 7,196,216 describes the conversion of gabapentin hydrochloride first to free base and then to its sulphate salt which is further treated with an inorganic base to obtain free gabapentin. The patent also describes the use of barium hydroxide as one of the inorganic bases which converts sulphate salt to free gabapentin. The process is cumbersome and involves a number of steps. Further use of barium hydroxide introduces toxic barium ions into the product at the final stages and requires extensive purification steps. Indian patent No. 186285 describes a process to convert gabapentin hydrochloride to gabapentin directly by treating with aqueous sodium hydroxide or other inorganic bases. U.S. Pat. Application No. US 2006/0149099 also describes a similar process and defines specific amounts of water and the alkali metal base to be used. Here, the reaction mixture is heated to 50-90° C., preferably at 60-70° C. This results in the formation of lactam to a significant extent and a method to recover lactam from the mother liquor is described (Mother liquor B, Example 1). Gabapentin obtained by these methods show high amounts of chloride, which is mainly from sodium chloride formed during neutralization with sodium hydroxide. Extensive purification steps are required to remove the chlorides.

Thus there is a need for a good process to convert gabapentin acid salt to free gabapentin which is free from anionic and other impurities.

SUMMARY OF THE INVENTION

Hitherto the approach has been to utilize a solvent in which either the gabapentin acid salt or the free gabapentin is soluble, so that when the salt is neutralized by an alkaline reagent, only one of them will be in solution and the other precipitated facilitating separation. This invariably depended on efficient solubility which influenced the overall recovery of the free gabapentin. In addition, none of these processes could efficiently remove the inorganic byproduct of the process from the resulting gabapentin. A solvent in which both the gabapentin acid salt and the free base are soluble but the alkali salt byproduct is insoluble might provide an alternative resulting in low inorganic anion content.

While studying the process described in U.S. Pat. No. 6,255,526 B1, we found that surprisingly benzyl alcohol dissolves both gabapentin acid salts and free gabapentin to a significant extent. Further experimentation with various solvents revealed that nitrobenzene also dissolves both gabapentin salts and free gabapentin to a significant extent.

We have utilized this unique property and have developed a novel, industrially useful process for the conversion of gabapentin hydrochloride and other salts to gabapentin. The invention avoids the disadvantages associated with the earlier methods. The process consists of dissolving gabapentin salt in benzyl alcohol or nitrobenzene and stirring the solution with finely powdered solid alkali base, which is not soluble in these solvents. Gabapentin acid salt reacts with the alkaline base and the gabapentin generated will remain in the solution. Inorganic salts, formed during the neutralization and being insoluble, are removed by filtration along with the excess alkali. The clear filtrate is treated with an anti-solvent, such as methyl t-butyl ether (MTBE), ethyl acetate (EtOAc), toluene, acetone or methylene chloride and the precipitated pure gabapentin is collected by filtration. It was found that the clear filtrate of benzyl alcohol or nitrobenzene can also be extracted with water. Pure gabapentin can be obtained by removing water under vacuum by evaporation or distillation.

DETAILED DESCRIPTION OF THE INVENTION

The present invention provides a process for the conversion of gabapentin acid salt to free gabapentin which comprises:
(i) treating gabapentin acid salt with an organic solvent in which both gabapentin salt and free gabapentin are soluble;
(ii) treating the organic phase with a solid anhydrous alkali base and stirring until the pH of the solution is 7.0 to 7.5;
(iii) filtering the solution to remove alkali salt formed during neutralization and any unreacted solid alkali and treating the filtrate with a suitable drying agent, if necessary, and filtering to remove the drying agent;
(iv) treating the filtrate with an anti-solvent to precipitate gabapentin free base, filtering the precipitate; and
(v) stirring gabapentin obtained in step (v) using a suitable alcoholic solvent.

Gabapentin hydrochloride can be prepared by one of the methods described in the literature, for example U.S. Pat. Nos. 4,024,175 or 4,152,326. Gabapentin sulphate can be prepared as described in U.S. Pat. No. 7,439,387 B2. It is dissolved in benzyl alcohol or nitrobenzene or in any other suitable organic solvent in which free gabapentin is also soluble. Such solvents being immiscible with water offer another important advantage. The aqueous solution of gabapentin hydrochloride obtained after Hoffmann rearrangement from cyclohexane diacetic acid monoamide (CDMA), in the popular route of synthesis, can be directly extracted from the reaction mixture with the selected solvent as for example benzyl alcohol or nitrobenzene. The solution is then treated with finely powdered solid alkali base such as sodium carbonate, potassium carbonate or potassium hydroxide and stirred till the solution is rendered neutral to pH. Gabapentin acid salt which is in solution reacts with the solid base in a biphasic manner. The liberated free gabapentin remains in solution and the inorganic salt such as sodium chloride formed during the neutralization is insoluble and is precipitated. The reaction is slow because of the biphasic nature of the reaction system and may take several hours for complete neutralization. Other bases in solid form, such as NaOH, KOH, LiOH, $Ca(OH)_2$, $Mg(OH)_2$, $Na_2CO_3$, $K_2CO_3$, $Li_2CO_3$, $CaCO_3$, $Ce_2CO_3$, $NaHCO_3$, $KHCO_3$ or mixtures containing these can also be used. The process was also successfully extended to gabapentin sulfate since it is also soluble in the selected solvents, such as benzyl alcohol and nitrobenzene. Filtering the solution removes the inorganic salt formed during the neutralization and also the unreacted alkali base. The clear filtrate is treated with an anti-solvent, such as methyl tert.butyl ether and the solution is stirred until gabapentin precipitates completely. Filtering the suspension gives gabapentin free base. Stirring at a lower temperature such as at 0-5° C. gives higher yields. The presence of moisture results in lower yields, which may be caused by the highly hygroscopic nature of some of the solid bases. One can overcome the problem of moisture in the solution by stirring the solution with a dehydrating agent, such as sodium sulfate, molecular sieves, etc.

Instead of treating with an anti-solvent, the filtrate can also be extracted with water. Gabapentin has a higher solubility in water than in benzyl alcohol or nitrobenzene and is easily extracted into water. Removal of water under reduced pressure gives gabapentin, which can be converted to the desired form by known methods.

Gabapentin obtained either by using anti-solvent or by extraction with water is stirred in alcoholic solvents, such as methanol (MeOH), ethanol, isopropyl alcohol (IPA), or a mixture of MeOH-IPA-water. This will help in removing the traces of benzyl alcohol and other impurities. This process directly yields the generic Form II polymorph of gabapentin of very high purity (>99.5%) and is free from anionic impurities. Since the reaction conditions are mild and efficient, the product obtained is completely free from the lactam impurity.

The embodiments of the present invention are further described in the following examples, which are not intended in any way to limit the scope of the invention.

Example-1

Gabapentin hydrochloride (50 g, 0.24 mol) was dissolved in benzyl alcohol (335 ml) at room temperature. Finely powdered sodium carbonate (25.4 g, 0.23 mol) was added, and the reaction mixture was stirred until the solution pH reaches 7.0 to 7.5. It will take about 2 to 3 hours. The suspension was filtered and the residue washed with about 15 ml benzyl alcohol. The clear filtrate was cooled to 0-5° C. and 700 ml of methyl tert.butyl ether (MTBE) was added. The solution was stirred for one hour and the precipitated gabapentin filtered. The crude gabapentin was washed with MTBE and stirred in ethanol to remove traces of benzyl alcohol to obtain pure gabapentin. Yield: 36.7 g (90%), HPLC: 99.7%, chloride content: 22 ppm, lactam content: 0.01%.

Example-2

Gabapentin hemi-sulfate hemihydrate (10 g, 0.043 mol) was dissolved in benzyl alcohol (70 ml) at room temperature. Finely powdered sodium carbonate (4.63 g, 0.043 mol) was added and the reaction mixture was stirred until the solution pH reaches 7.0 to 7.5. It will take about 2 to 3 hours. The suspension filtered and the residue washed with about 5 ml benzyl alcohol. The clear filtrate was cooled to 0-5° C. and 140 ml of methyl tert.butyl ether (MTBE) was added. The solution was stirred for one hour and the precipitated gabapentin filtered. The crude gabapentin was washed with MTBE and stirred in ethanol to remove traces of benzyl alcohol to obtain pure gabapentin. Yield: 5.49 g (73.5%), HPLC: 99.5%.

Example-3

Gabapentin hydrochloride (10 g, 0.048 mol) was dissolved in benzyl alcohol (70 ml) at room temperature. Finely powdered potassium hydroxide (2.7 g, 0.048 mol) was added and the reaction mixture was stirred till the solution pH reaches 7.0 to 7.5. It will take about 2 to 3 hours. The suspension was filtered and the residue washed with about 5 ml benzyl alcohol. The clear filtrate was cooled to 0-5° C. and 140 ml of methyl tert.butyl ether (MTBE) was added. The solution was stirred for one hour and the precipitated gabapentin filtered. The crude gabapentin was washed with MTBE and stirred in ethanol to remove traces of benzyl alcohol to obtain pure gabapentin. Yield: 6.9 g (84%), HPLC: 99.6%.

Example-4

Gabapentin hemi-sulphate hemihydrate (10 g, 0.043 mol) was dissolved in nitrobenzene (100 ml) at room temperature. Finely powdered potassium carbonate (6.04 g, 0.043) was added and the reaction mixture was stirred until the solution pH reaches 7.0 to 7.5. After about 2 to 3 hours the suspension was filtered and the residue washed with about 5 ml nitrobenzene. The clear filtrate was cooled to 0-5° C. and 150 ml of methyl tert.butyl ether (MTBE) was added. The solution was stirred for one hour and the precipitated gabapentin filtered. The crude gabapentin was washed with MTBE and stirred in ethanol to remove traces of benzyl alcohol to obtain pure gabapentin. Yield: 4.56 g (61%), HPLC: 99.6%.

Example-5

Gabapentin hydrochloride (10 g, 0.048 mol) was dissolved in benzyl alcohol (70 ml) at room temperature. Finely powdered potassium carbonate (6.65 g, 0.048 mol) was added and the reaction mixture was stirred until the pH of solution reaches 7.0 to 7.5. After about 2 to 3 hours the suspension was filtered and the residue washed with about 5 ml benzyl alcohol. Filtrate was extracted with water (30 ml×2). Water layer was washed with ethyl acetate to remove traces of benzyl alcohol. The aqueous layer was concentrated under reduced pressure at 45° C. to obtain crude gabapentin. Stirring in ethanol resulted in pure gabapentin. Yield: 6.5 g (79%), HPLC: 99.8%.

Example-6

Cyclohexane diaceticacid monoamide (20 g, 0.1 mol) was dissolved in 4 N NaOH solution (30 ml) at 15-20° C. To this 100 ml of a solution of 7-8% sodium hypochlorite and 10.2 g sodium hydroxide were added and stirred for 5 h. Excess hypochlorite was neutralized by 1 g sodium metabisulphite solution. The solution was acidified to pH 2 by HCl. The aqueous solution was extracted with benzyl alcohol (40 ml×2). The organic layer was dried over anhydrous $Na_2SO_4$. Finely powdered sodium carbonate (10.65 g, 0.1 mol) was added and the reaction mixture was stirred until the solution pH reaches 7.0 to 7.5. It will take about 2 to 3 hours. The suspension was filtered and the residue washed with about 5 ml benzyl alcohol. The clear filtrate was cooled to 0-5° C. and 160 ml of methyl tert.butyl ether (MTBE) was added. The solution was stirred for one hour and the precipitated gabapentin filtered. The crude gabapentin was washed with MTBE and stirred in ethanol to remove traces of benzyl alcohol to obtain pure gabapentin. Yield: 11.8 g (68.6% based on CDMA), HPLC: 99.6%.

Example-7

Cyclohexane diaceticacid monoamide (20 g, 0.1 mol) was dissolved in 4N NaOH solution (30 ml) at 15-20° C. To this 100 ml solution of 7-8% sodium hypochlorite and 10.2 g sodium hydroxide were added and stirred for 5 h. Excess hypochlorite was neutralized by 1 g sodium metabisulphite solution. The solution was acidified to pH 2 by HCl. The aqueous solution was extracted with benzyl alcohol (40 ml×2). The organic layer was dried over anhydrous $Na_2SO_4$. Finely powdered sodium carbonate (10.65 g, 0.1 mol) was added and the reaction mixture was stirred until the solution pH reaches 7.0 to 7.5. It will take about 2 to 3 hours. The suspension filtered and the residue washed with about 5 ml benzyl alcohol. The organic solution was extracted with water (60 ml). The layer was separated and washed with ethyl acetate to remove traces of benzyl alcohol.

The aqueous layer was concentrated to obtain crude gabapentin. Stirring in ethanol resulted in pure gabapentin. Yield: 10.14 g (59% based on CDMA), HPLC: 99.6%.

Without further elaboration the foregoing will so fully illustrate our invention that others may, by applying current or future knowledge, adopt the same for use under various conditions of service.

We claim:

1. A process for the preparation of gabapentin free base which comprises:
    i) treating gabapentin acid salt with an organic solvent in which both the gabapentin salt and free gabapentin are soluble to obtain an organic phase;
    ii) treating the organic phase with a solid anhydrous alkali base and stirring until the pH is 7.0 to 7.5;
    iii) filtering the solution of step (ii) to remove alkali salt formed during neutralization in step (ii) and any unreacted solid alkali and optionally treating the filtrate with a suitable drying agent and then filtering to remove the drying agent,
    iv) treating the filtrate of step (iii) with an anti-solvent to precipitate gabapentin free base and filtering the precipitate; and
    v) stirring the gabapentin obtained in step (v) with a suitable alcoholic solvent.

2. A process as in claim 1 in which the gabapentin acid salt in step (i) is present in a reaction mixture formed from any of its precursors.

3. A process as in claim 1, step (i) wherein the acid salt is gabapentin hydrochloride.

4. A process as in claim 1, step (i) wherein the acid salt is gabapentin sulfate or gabapentin hemisulfate.

5. A process as in claim 1, step (i), wherein the organic solvent is benzyl alcohol.

6. A process as in claim 1, step (i), wherein the organic solvent is nitrobenzene.

7. A process as in claim 1, step (ii), wherein the alkali base used is selected from the group consisting of sodium hydroxide, potassium hydroxide, lithium hydroxide, calcium hydroxide, magnesium hydroxide, sodium carbonate, potassium carbonate, lithium carbonate, calcium carbonate, cesium carbonate, sodium bicarbonate, potassium bicarbonate or mixtures thereof.

8. A process as in claim 1, step (v), wherein the anti-solvent is selected from the group consisting of methyl t-butyl ether, ethyl acetate, toluene, acetone and methylene chloride.

9. A process as in claim 8, where the anti-solvent is methyl t-butyl ether.

10. A process as in claim 1, step (v) wherein the filtrate from step (iv), instead of being treated with an anti-solvent, is extracted with water followed by removal of the water under reduced pressure to obtain gabapentin free base.

11. A process as in claim 1, step (iii), wherein the drying agent is sodium sulfate.

12. A process as in claim 1, step (v), wherein the alcoholic solvent is methanol, ethanol or isopropyl alcohol.

* * * * *